United States Patent
Matsuzawa et al.

(10) Patent No.: US 11,491,116 B2
(45) Date of Patent: Nov. 8, 2022

(54) ADHESIVE PATCH

(71) Applicant: LEAD CHEMICAL CO., LTD., Toyama (JP)

(72) Inventors: Takayasu Matsuzawa, Toyama (JP); Seijiro Yama, Toyama (JP); Naoki Murai, Toyama (JP)

(73) Assignee: LEAD CHEMICAL CO., LTD., Toyama (JP)

( * ) Notice: Subject to any disclaimer, the term of this patent is extended or adjusted under 35 U.S.C. 154(b) by 710 days.

(21) Appl. No.: 16/085,048

(22) PCT Filed: Mar. 16, 2016

(86) PCT No.: PCT/JP2016/058349
§ 371 (c)(1),
(2) Date: Oct. 22, 2018

(87) PCT Pub. No.: WO2017/158766
PCT Pub. Date: Sep. 21, 2017

(65) Prior Publication Data
US 2019/0046464 A1 Feb. 14, 2019

(51) Int. Cl.
*A61K 9/70* (2006.01)
*A61F 13/02* (2006.01)
*A61F 13/00* (2006.01)

(52) U.S. Cl.
CPC ........ *A61K 9/703* (2013.01); *A61F 13/00059* (2013.01); *A61F 13/023* (2013.01); *A61K 9/70* (2013.01); *A61F 2013/0296* (2013.01)

(58) Field of Classification Search
CPC ..... A61K 9/703; A61K 9/70; A61F 13/00059; A61F 13/023; A61F 2013/0296; A61F 13/00063; A61F 2013/00238; A61F 2013/00327; A61F 2013/00574; A61F 2013/00646
See application file for complete search history.

(56) References Cited

U.S. PATENT DOCUMENTS

| 4,237,889 A | 12/1980 | Gobran |
| 2002/0110585 A1 | 8/2002 | Godbey et al. |
| 2007/0232979 A1 | 10/2007 | Montgomery |

FOREIGN PATENT DOCUMENTS

| JP | S63-175128 U | 11/1988 |
| JP | H07-126156 A | 5/1995 |
| JP | H08-103982 A | 4/1996 |
| JP | H08-257058 A | 10/1996 |
| JP | 2001-231812 A | 8/2001 |
| JP | 3155463 U | 11/2009 |
| KR | 95-3983 U | 5/1995 |
| WO | 98/29231 A1 | 7/1998 |

OTHER PUBLICATIONS

Aug. 14, 2019 extended European Search Report issued in European Patent Application No. 16894384.3.
Apr. 13, 2021 Office Action issued in European Application No. 16 894 384.3.
May 20, 2020 Office Action issued in European Patent Application No. 16894384.3.
Jun. 7, 2016 International Search Report issued in International Patent Application No. PCT/JP2016/058349.
Jun. 7, 2016 Written Opinion issued in International Patent Application No. PCT/JP2016/058349.
Aug. 22, 2022 Office Action issued in Korean Application No. 10-2018-7029256.

*Primary Examiner* — Hasan S Ahmed
(74) *Attorney, Agent, or Firm* — Oliff PLC

(57) ABSTRACT

An adhesive patch comprising: a support; at least a pressure-sensitive adhesive layer provided on the support; and a release liner attached on the pressure-sensitive adhesive layer so as to cover the surface of the pressure-sensitive adhesive layer, in which the support is a 3D patterned sheet characterized in that a plurality of protruded lines and recessed lines parallelly and linearly extending are formed inside and outside lines in a plurality of figures partitioned by the lines, walls of the protruded lines and recessed lines in some of the figures are formed to be inclined by different inclination angles with respect to a base part, and the protruded lines have different heights from the base part, serving as physical parameters of the protruded lines and recessed lines, toward a predetermined direction in the sheet.

6 Claims, 8 Drawing Sheets

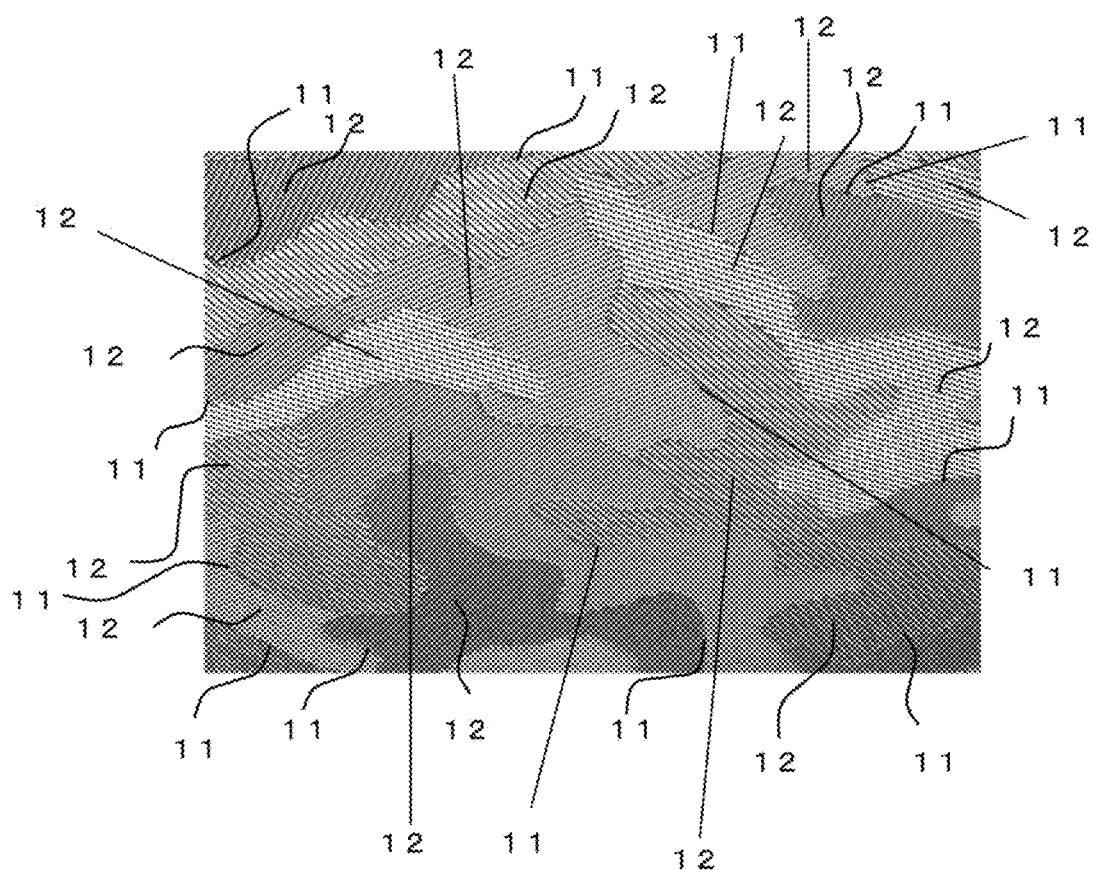
[FIG. 1A]
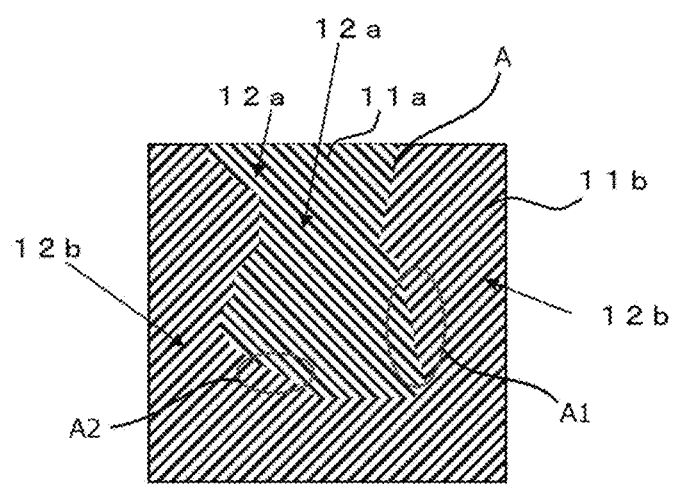
[FIG. 1B]

[FIG. 2]
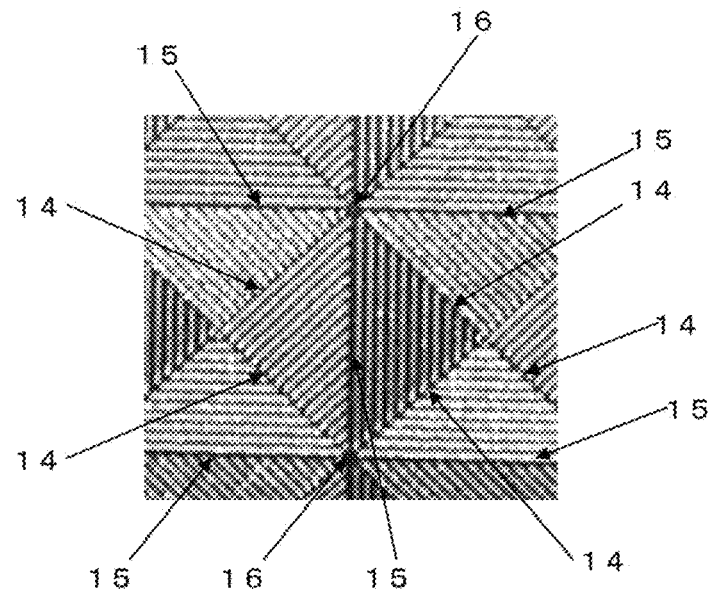
[FIG. 3A]             [FIG. 3B]
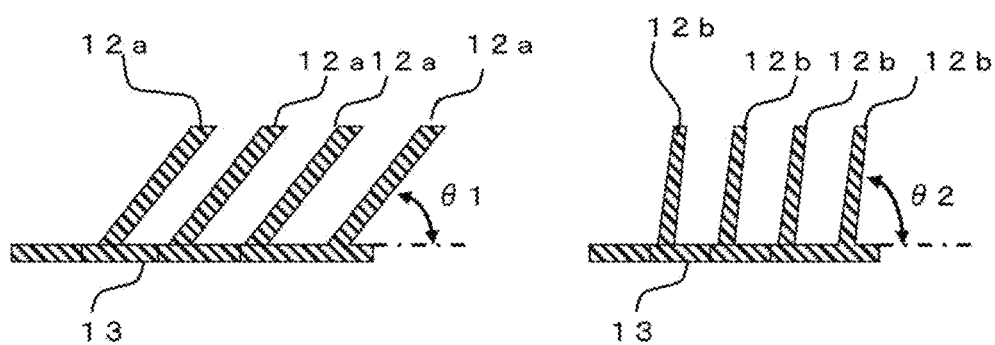

[FIG. 4]
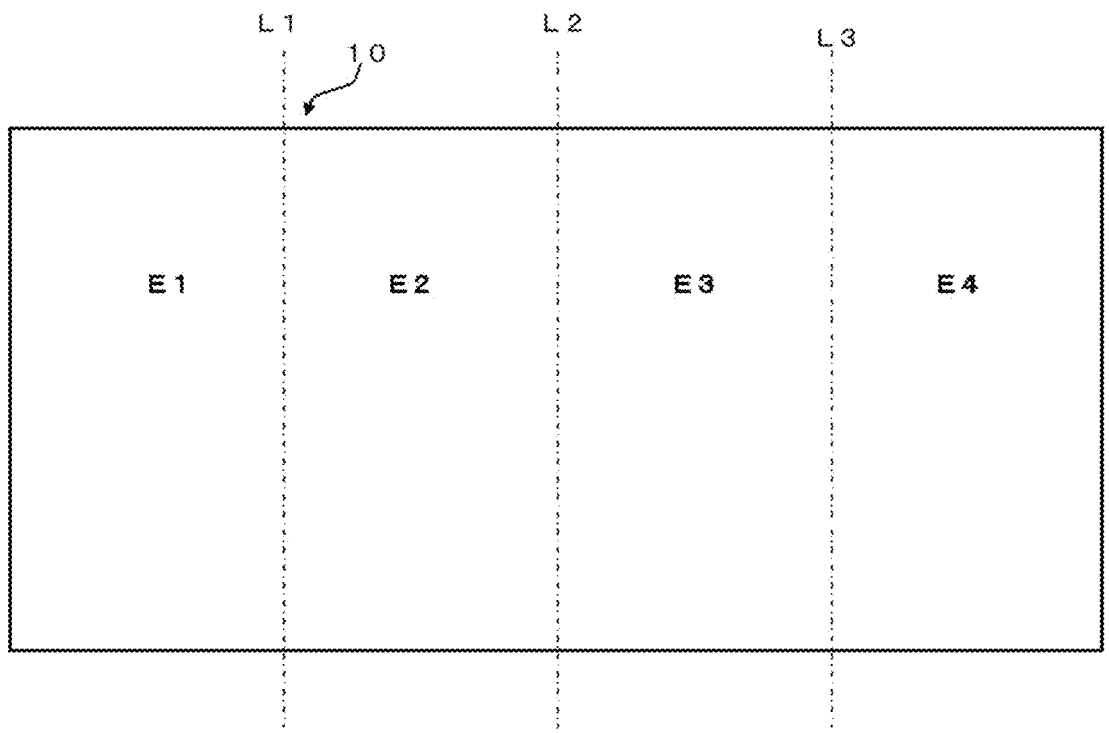
[FIG. 5]
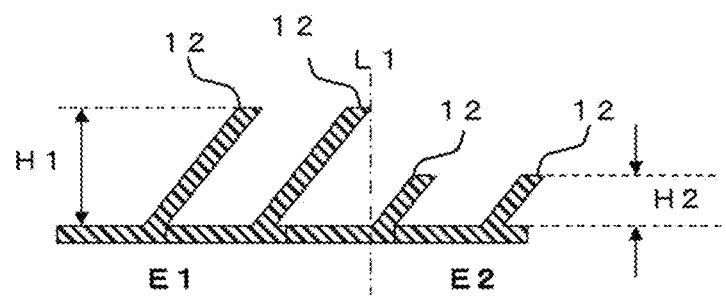

[FIG. 6]
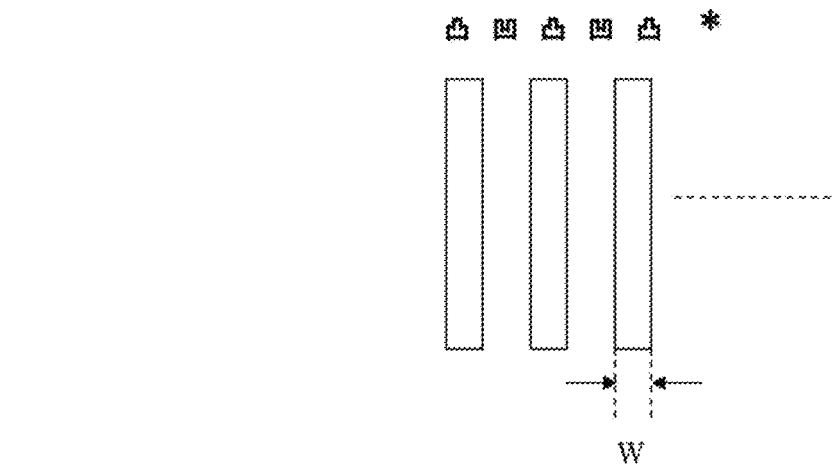
* 凸 PROTRUDED LINE
  凹 RECESSED LINE
[FIG. 7]
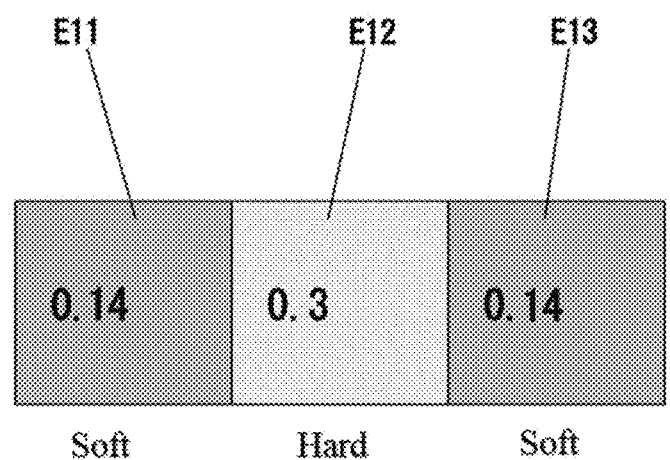

[FIG. 8]
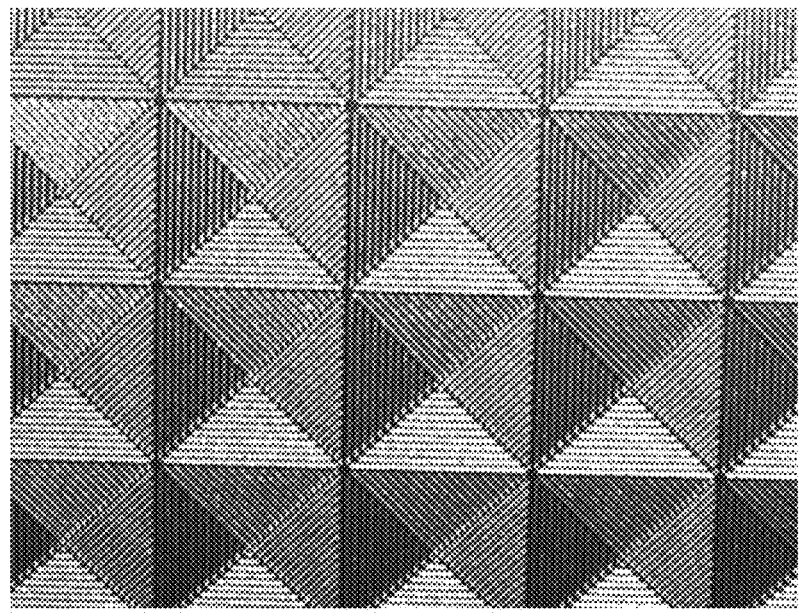
[FIG. 9]
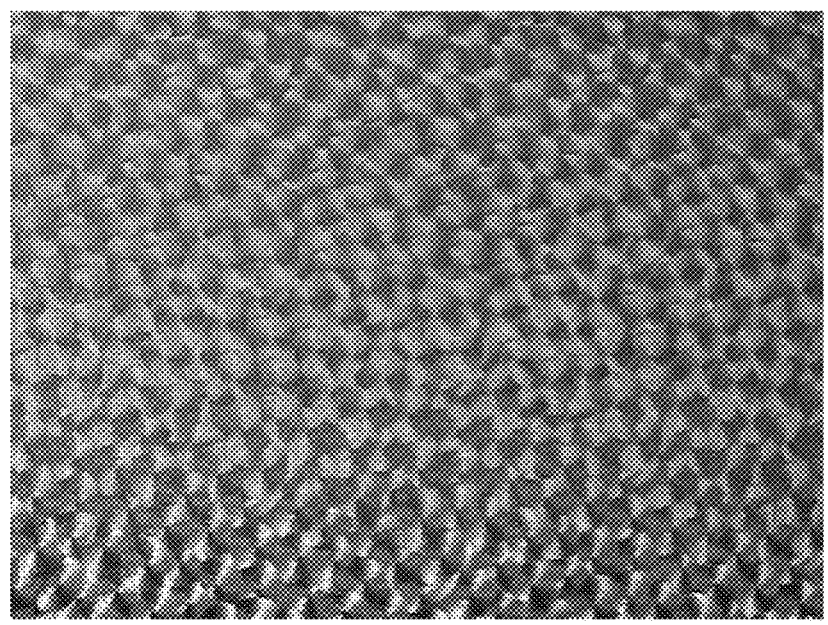

[FIG. 10]
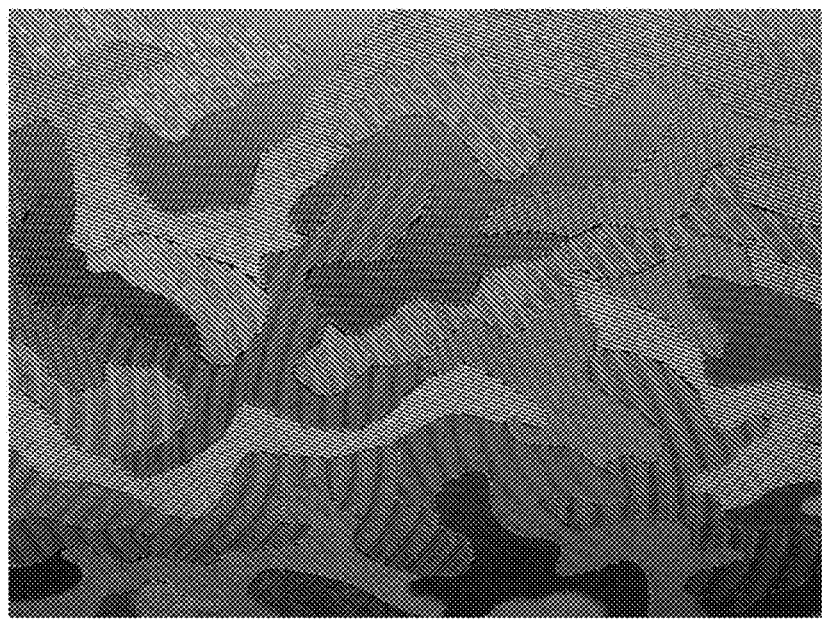
[FIG. 11]
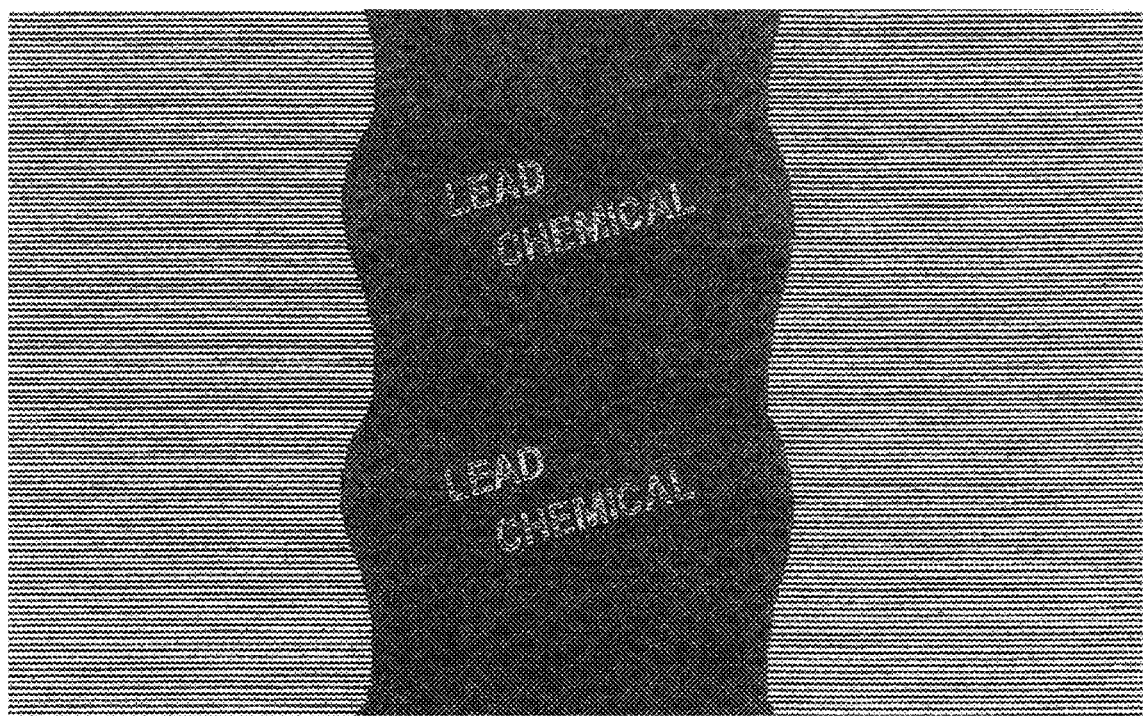

[FIG. 12]
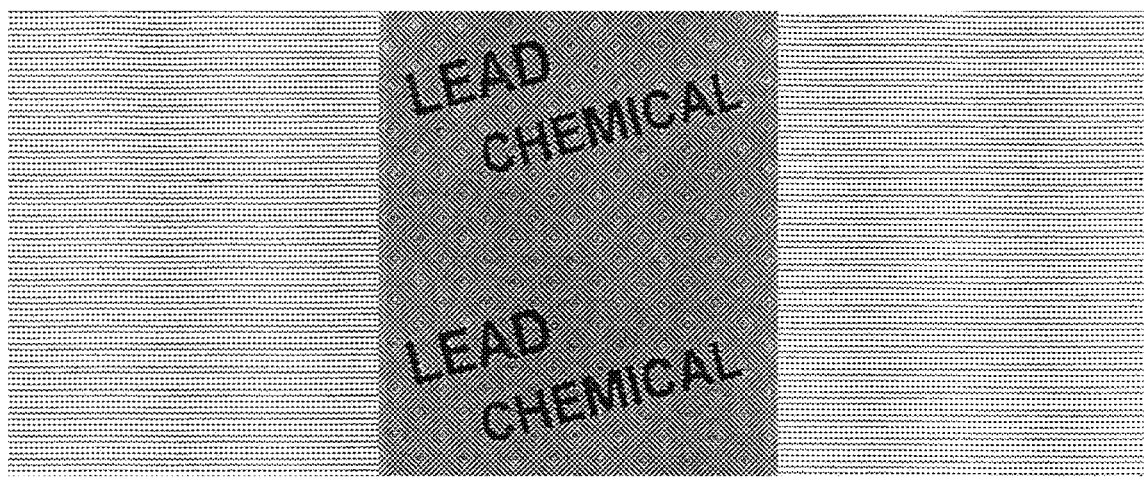
[FIG. 13]
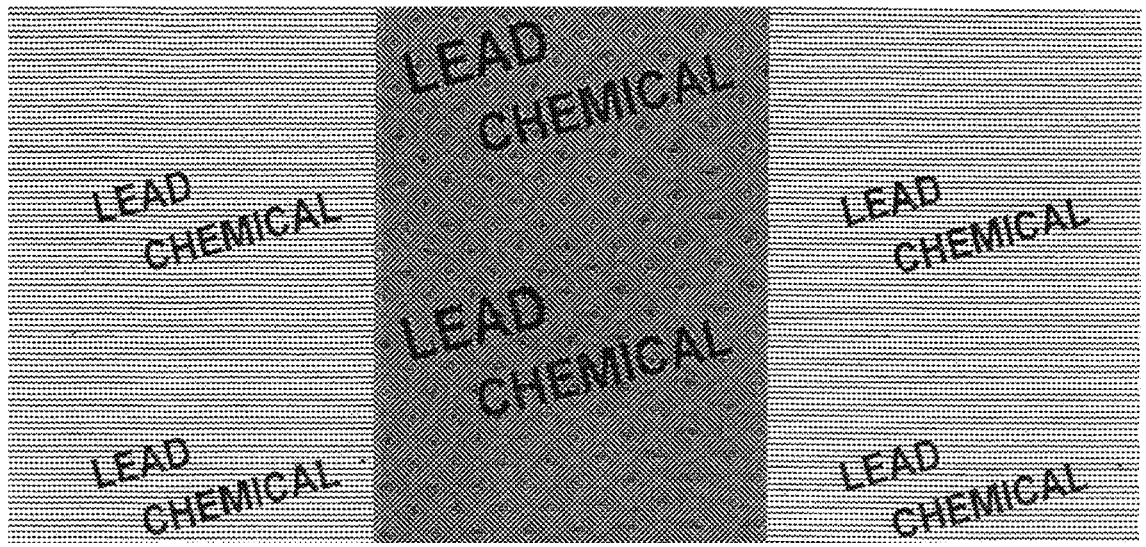

[FIG. 14]
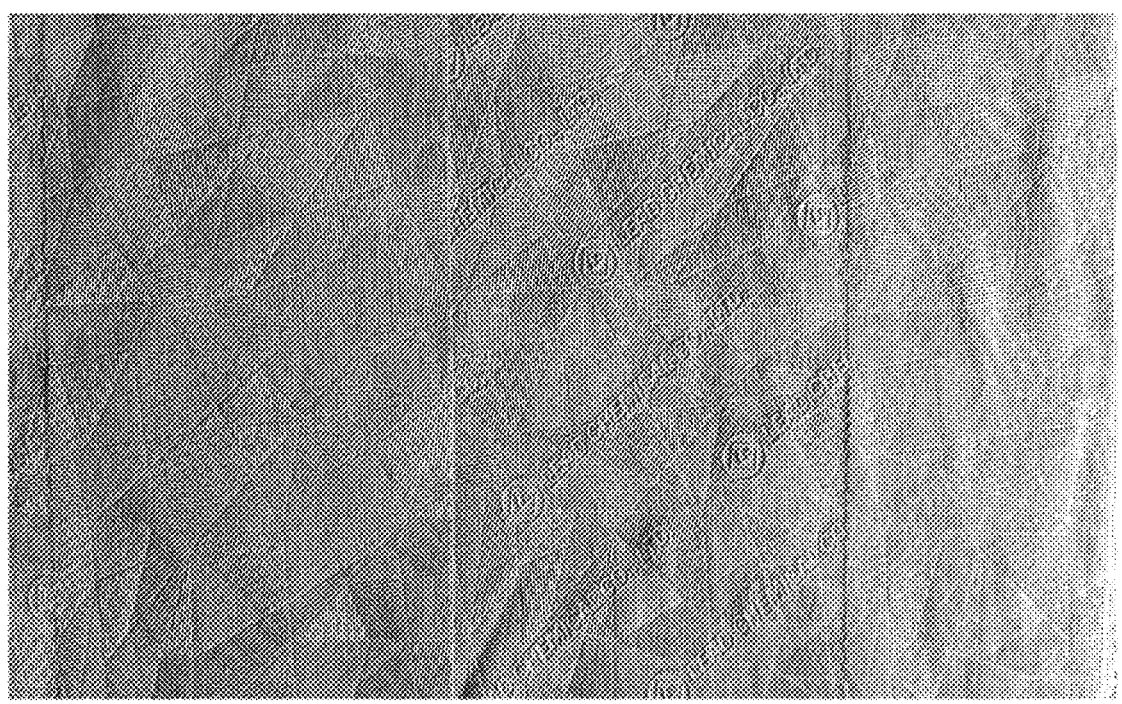

ADHESIVE PATCH

TECHNICAL FIELD

The present invention relates to an adhesive patch, and particularly relates to an adhesive patch using a 3D patterned sheet of which the provided pattern varies its appearance depending on a viewing direction and the pattern appears three-dimensionally as the support of the adhesive patch.

BACKGROUND ART

An adhesive patch applied as a percutaneous absorption external preparation is generally provided as an adhesive patch product including the adhesive patch and a package formed by hermetically packaging the adhesive patch.

Generally, in the package of the adhesive patch product, the kind of the adhesive patch (medicine name and the like) contained in the package, the effect and efficacy of the adhesive patch, application methods (attaching method, application frequency, and the like), and the like are described. In accordance with this description, medicine providers and medicine users are checking the kind and usage of the adhesive patch. Furthermore, improved products have been developed so that, even after the adhesive patch is taken out from the package of the adhesive patch product, the kind and application method of the adhesive patch can be distinguished due to description of the name, kind, and usage of the adhesive patch by printing or the like on the surface of a release liner or a support.

In order to distinguish the kind and name of the adhesive patch or to facilitate taking out the adhesive patch from a package and putting it into the package, application of unevenness (emboss) processing to the surface of a release liner or a support has been developed (refer to Patent Document 1 to Patent Document 3).

On the other hand, an embossing roll on which the fine line grooves in a plurality of patterns having different cutting angles, cutting widths, densities, and cutting depths are formed by irradiation with laser beams on the outer peripheral surface of the roll main body has been developed (refer to Patent Document 4).

PRIOR ART DOCUMENTS

Patent Document

Patent Document 1: Japanese Patent Application Publication No. H07-126156 (JP H07-126156 A)
Patent Document 2: Japanese Patent Application Publication No. S63-175128 (JP S63-175128 A)
Patent Document 3: Japanese Patent Application Publication No. 2001-231812 (JP 2001-231812 A)
Patent Document 4: Japanese Utility Registration Model No. 3155463

SUMMARY OF THE INVENTION

Problem to be Solved by the Invention

As described in Patent Documents 1 to 3, an adhesive patch in which simple emboss processing is applied to the surface of the support, that is, the surface opposite to the surface in contact with a pressure-sensitive adhesive layer has been developed.

On the other hand, in the embossing roll described in Patent Document 4, the fine line grooves in a plurality of patterns are formed on the outer peripheral surface of the roll main body by laser beam irradiation and the 3D patterned sheet on which the fine line grooves are transferred can be produced. However, no development has yet to be made for a 3D patterned sheet in which making a difference in appearance for each part is considered and artistic patterns appealing to the eyesight of the viewer are provided. Furthermore, the adhesive patch using such a 3D patterned sheet as a support has yet to be developed.

Means for Solving the Problem

The inventors of the present invention have studied employment of a 3D patterned sheet that has yet to be employed as the support of an adhesive patch. First, the inventors of the present invention have found that the rigidity (flexibility) of the sheet can be controlled by adequately selecting the physical parameters such as the height of the protruded lines and the width of protruded lines and recessed lines that are formed as fine line grooves on the 3D patterned sheet. The inventors of the present invention have found that the 3D patterned sheet that can easily change the flexibility depending on each part requiring rigidity or flexibility and for which the final product having suitable human sense and sensibility of touch and texture is considered is obtained by varying the physical parameters of the protruded lines and recessed lines in the sheet and an adhesive patch having excellent design and excellent usability during use is obtained by using the 3D patterned sheet as the support of the adhesive patch. Thus, the inventors of the present invention have accomplished the present invention.

Therefore, the present invention relates to an adhesive patch comprising:
  a support;
  at least a pressure-sensitive adhesive layer provided on the support; and
  a release liner attached on the pressure-sensitive adhesive layer so as to cover the surface of the pressure-sensitive adhesive layer,
  in which the support is a 3D patterned sheet characterized in that a plurality of protruded lines and recessed lines parallelly and linearly extending are formed inside and outside lines in a plurality of figures partitioned by the lines,
  walls of the protruded lines and recessed lines in some of the figures are formed to be inclined by different inclination angles with respect to a base part, and
  the protruded lines have different heights from the base part, serving as physical parameters of the protruded lines and recessed lines, toward a predetermined direction in the sheet.

In the adhesive patch according to the present invention, the physical parameters of the 3D patterned sheet are preferably constituted of the widths of the protruded lines and recessed lines, the inclination angles, the densities of the lines formed by the protruded lines and recessed lines, and a heating temperature in 3D pattern processing in addition to the heights of the protruded lines, and at least one of the physical parameters is preferably different from each other.

In the adhesive patch according to the present invention, the 3D patterned sheet is preferably divided into a plurality of regions toward a predetermined direction in the sheet, and at least one of the physical parameters is preferably different from each other in adjacent regions.

In the adhesive patch according to the present invention, the 3D patterned sheet is preferably divided into a plurality of regions by line segments orthogonal in the surface of the sheet to a line heading toward a predetermined direction in the sheet.

In the adhesive patch according to the present invention, the 3D patterned sheet is preferably formed so that one surface of the sheet is determined to be a front surface and the other surface is determined to be a back surface, the front surface having a pattern formed by protruded lines and recessed lines, the back surface being smooth, and the pressure-sensitive adhesive layer being provided on the back surface.

In the adhesive patch according to the present invention, the support including the 3D patterned sheet is particularly preferably formed of a knitted fabric, a woven fabric, or a nonwoven fabric made of fibers of at least one thermoplastic resin selected from the group consisting of a polyester-based resin, a polyamide-based resin, an acetyl cellulose-based resin, and a polylactic acid-based resin.

Effects of the Invention

In the adhesive patch according to the present invention, the 3D patterned sheet produced by varying the heights of the protruded lines from the base part toward the predetermined direction in the sheet is used as the support. Application of the adhesive patch onto a human skin allows artistic appearance of the adhesive patch to be different depending on a direction to be seen or a part to be seen and the touch to be also excellent.

In the adhesive patch according to the present invention, not only the kind of the adhesive patch (for example, an included medicine) and a method for applying the adhesive patch can be distinguished by changing the 3D pattern of the support but also the kind of the adhesive patch and the included medicine can be distinguished during the application onto the skin. Consequently, this adhesive patch can prevent inappropriate use and abuse.

The adhesive patch according to the present invention allows the kind of the adhesive patch (a formulated medicine, an application method, and the like) to be distinguished by the 3D pattern provided in the 3D patterned sheet used as the support. Consequently, the adhesive patch does not cause problems by printing using ink, that is, contamination to the pressure-sensitive adhesive layer (medicine-containing layer) due to penetration of the ink into the inside of a sheet made of a nonwoven fabric and the like used as the support and occurrence of bleeding at the printed place on the surface of the support (a nonwoven fabric) due to penetration of the component included in the pressure-sensitive adhesive layer into the inside of the support (a nonwoven fabric and the like).

BRIEF DESCRIPTION OF THE DRAWINGS

FIGS. 1A and 1B are views illustrating one aspect of a 3D patterned sheet used as the support of the adhesive patch according to the present invention. FIG. 1A is the plan view of the 3D patterned sheet and FIG. 1B is the enlarged plan view of a part of the 3D patterned sheet.

FIG. 2 is a view illustrating another aspect of the 3D patterned sheet used as the support of the adhesive patch according to the present invention and a view illustrating an enlarged plan view of a part of the 3D patterned sheet.

FIGS. 3A and 3B are views illustrating the section of the 3D patterned sheet used as the support of the adhesive patch according to the present invention and are sectional views each illustrating the cases where the side walls of protruded lines and recessed lines are formed so as to have an angle $\theta 1$ (FIG. 3A) and have an angle $\theta 2$ (FIG. 3B) with respect to a base part.

FIG. 4 is a plan view illustrating one example of the 3D patterned sheet used as the support of the adhesive patch according to the present invention that has partitioned regions in the longitudinal direction of the sheet.

FIG. 5 is a sectional view of one example of the 3D patterned sheet used as the support of the adhesive patch according to the present invention in which the protruded lines and recessed lines are formed in the partitioned region so as to have different heights.

FIG. 6 is an enlarged plan view enlarging the protruded lines and recessed lines of the 3D patterned sheet used as the support of the adhesive patch according to the present invention.

FIG. 7 is a plan view illustrating one example of the 3D patterned sheet used as the support of the adhesive patch according to the present invention that has partitioned regions in the longitudinal direction of the sheet.

FIG. 8 is a view illustrating the 3D pattern of the 3D patterned sheet used as the support of the adhesive patch prepared in Examples.

FIG. 9 is a view illustrating the 3D pattern of the 3D patterned sheet used as the support of the adhesive patch prepared in Examples.

FIG. 10 is a view illustrating the 3D pattern of the 3D patterned sheet being the support of the adhesive patch prepared in Examples.

FIG. 11 is a view illustrating the 3D pattern of the 3D patterned sheet used as the support of the adhesive patch prepared in Examples.

FIG. 12 is a view illustrating the 3D pattern of the 3D patterned sheet used as the support of the adhesive patch prepared in Examples.

FIG. 13 is a view illustrating the 3D pattern of the 3D patterned sheet used as the support of the adhesive patch prepared in Examples.

FIG. 14 is a view illustrating the 3D pattern of the 3D patterned sheet used as the support of the adhesive patch prepared in Examples.

MODES FOR CARRYING OUT THE INVENTION

The present invention targets an adhesive patch including a support; at least a pressure-sensitive adhesive layer provided on the support; and a release liner attached on the pressure-sensitive adhesive layer so as to cover the surface of the pressure-sensitive adhesive layer. Formulations such as cataplasms and plasters can be applied to the adhesive patch targeted by the present invention.

Hereinafter, each layer constituting the adhesive patch according to the present invention will be described in detail.

Support

The 3D patterned sheet is used as the support in the adhesive patch according to the present invention. Hereinafter, the 3D patterned sheet will be described with reference to the attached drawings. In each of the drawings, the same reference numerals are assigned to the same constituent elements and redundant descriptions are omitted.

In the present invention, the term "3D patterned sheet" collectively refers to sheets that provide the protruded lines and recessed lines (embossment) different for each region (figure), whereby the appearance of the protruded lines and recessed lines (embossment) is different for each region (figure) and different visual effects depending on the viewing direction and the viewing part are intended to be obtained.

In FIGS. 1A and 1B, a plan view of one aspect of the 3D patterned sheet used as the support of the adhesive patch according to the present invention (FIG. 1A) and an enlarged plan view of a part of the sheet (FIG. 1B) are illustrated. The 3D patterned sheet includes a plurality of FIGS. 11 partitioned by lines. The outline of this FIG. 11 indicates the range of the figure. The FIG. 11 may include a part to which the number 11 is not assigned and may also refer to a part of the substrate of the sheet.

As illustrated in FIG. 1B, the figures partitioned by the lines indicate figures divided into several parts by the boundary A. The figure according to the present invention may also include "representation of characters by a figure" and this "representation of characters by a figure" can express, for example, a logo in the sheet.

On the inside and outside of the profile line in the FIG. 11 illustrated in FIG. 1, a plurality of linearly extending protruded lines and recessed lines 12 are formed in parallel. More specifically, as illustrated in FIG. 1B, emboss processing is applied on the surface of the 3D patterned sheet (that is, the support of the adhesive patch according to the present invention) in the adjacent figures divided by the boundary A so that a plurality of lines is formed in parallel.

As illustrated in the enlarged plan view of FIG. 1B, the length direction of the protruded lines and recessed lines 12a of the FIG. 11a and the length direction of the protruded lines and recessed lines 12b of the FIG. 11b are formed in different directions. In the aspect illustrated in FIG. 1B, these protruded lines and recessed lines are formed in directions orthogonal to each other. In other words, as illustrated in FIG. 1B, the embossments (12a, 12b) linearly and parallelly processed are not parallel to each other but have different directions in the adjacent figures divided by the boundary A.

In the 3D patterned sheet according to this aspect, the boundary A between the FIG. 11a and the FIG. 11b is formed in one aspect of the 3D patterned sheet by oppositely abutting the terminal end in the longitudinal direction of the protruded lines and recessed lines 12a in the FIG. 11a and the terminal end in the longitudinal direction of the protruded lines and recessed lines 12b in the FIG. 11b (refer to the part (A1) in FIG. 1B). The boundary A between the FIG. 11a and the FIG. 11b in another aspect is formed by abutting the side surfaces of the protruded lines and recessed lines 12a (12b) in the FIG. 11a (11b) and the terminal end in the longitudinal direction of the protruded lines and recessed lines 12b (12a) in the FIG. 11b (11a) (refer to the part (A2) in FIG. 1B).

In addition to the aspects illustrated in FIGS. 1A and 1B, the embossment (protruded lines) linearly extending in the boundary A of the 3D patterned sheet may include aligned linear embossment or curved embossment or a combination thereof.

The 3D patterned sheet may include not only the linearly extending embossment but also protruded parts (protruded lines) formed of dots, figures such as circles, quadrangles, and triangles, and character strings and figures formed by combining these dots, figures, and character strings with each other.

FIG. 2 is an enlarged plan view illustrating another aspect of the 3D patterned sheet used as the support of the adhesive patch according to the present invention.

As illustrated in FIG. 2, the 3D patterned sheet of this aspect has a substantially square region (figure) divided into a downwardly protruded triangular region (figure), an upwardly protruded triangular region (figure), a region (figure) protruding to right, and a region (figure) protruding to left. This divided square forms a one-unit region (figure). A pattern is formed by forming a plurality of protruded lines and recessed lines in each triangular region (figure) in a one-unit region (figure). In the one-unit region (figure), that is, in the substantially square area (figure) formed of the regions of the four triangles (figures), the boundary 14 formed by mutually abutting the protruded lines and recessed lines is formed similar to the boundary A previously described in FIG. 1B. The 3D patterned sheet of this aspect is formed by repeatedly forming the one-unit regions (the figures, that is, the pattern) in the upper, lower, left, and right directions. Grooves are formed in the boundary lines 15 where the one-unit regions (the figures, that is, the pattern) are adjacent to each other. A collection point 6 of the four boundary lines 15 generated by collecting the four one-unit regions (the figures, that is, the pattern) is not defined as a groove but defined as a protruded part.

On the surface of the 3D patterned sheet used as the support of the adhesive patch according to the present invention, the walls of the protruded lines and recessed lines 12 are formed to be inclined by different inclination angles with respect to the base part in some of the FIG. 11. The term "base part" refers to the surface of the 3D patterned sheet (support). The phrase "is formed to be inclined by different inclination angles with respect to the base part" means that the protruded lines are formed so that the walls of the protruded lines have various inclination angles with respect to the base surface.

For example, each of the walls of the protruded lines and recessed lines 12 is formed so that the inclination angle $\theta1$ of the protruded lines and recessed lines 12a in the FIG. 11a (not illustrated in FIG. 3) with respect to the base part 13 (that is, the inclination $\theta1$ of the protruded lines with respect to the base part 13) as illustrated in FIG. 3A and the inclination angle $\theta2$ of the protruded lines and recessed lines 12b in the FIG. 11b (not illustrated in FIG. 3) with respect to the base part 13 (that is, the inclination $\theta2$ of the protruded line part with respect to the base part 1) as illustrated in FIG. 3B are different.

As described above, a constitution in which at least two kinds of inclination angles ($\theta1$ and $\theta2$) are prepared, a first inclination angle ($\theta1$) may be applied to some of the FIG. 11 of the 3D patterned sheet, and the second inclination angle ($\theta2$) is applied to the remaining FIG. 11 may be employed. As a matter of course, a constitution in which three or more inclination angles ($f1, \theta2, \theta3, \ldots$, and the like) are applied may be employed.

In one FIG. 11, an aspect including the protruded lines formed so that the walls of the protruded lines have not only the first inclination angle alone with respect to the base part 13 (the surface) but also the protruded lines formed so as to have the second inclination angle in addition to the protruded lines formed with the first inclination angle may be employed.

In the 3D patterned sheet used as the support of the adhesive patch according to the present invention, the protruded lines and recessed lines 12 are formed so as to have different heights, serving as the physical parameter of the protruded lines and recessed lines 2, from the base part 13 toward the predetermined direction in the sheet. The "predetermined direction" means the longitudinal direction or the lateral direction of the sheet, or the oblique direction provided with respect to the longitudinal direction (or the lateral direction). A plurality of regions is provided for each of these directions and the protruded lines and recessed lines (embossment) are formed so that the protruded lines have different heights from the base part (sheet surface) of the sheet in adjacent regions. The regions provided for the predetermined direction may be the same as or different from the figures divided by the boundary as illustrated by the above boundary 14 and the like.

In the present invention, a line segment orthogonal to a straight line heading toward a predetermined direction in the plane of the sheet refers to a line segment orthogonal to the longitudinal direction (that is, in the lateral direction) of the sheet, a line segment orthogonal to the lateral direction (that is, in the longitudinal direction) of the sheet, and a line segment orthogonal to the oblique direction of the sheet, for example, orthogonal to a 45 degree direction (that is, in the reverse oblique direction of 45 degrees).

For example, as illustrated in FIG. 4, a sheet 10 is partitioned into four regions E1 to E4 in the longitudinal direction by lines L1, L2, and L3 orthogonal to the lateral direction of the sheet 10. For example, H1 and H2 are prepared as the heights of the protruded lines and recessed lines 12 from the base part 13 (the heights of the protruded lines from the base part). The height H1 is employed in the regions E1 and E3 and the height H2 is employed in the regions E2 and E4. This allows a configuration having different heights of the protruded lines and recessed lines 12 from the base part 13 (heights of the protruded lines from the base part) in the adjacent regions to be formed.

FIG. 5 is a sectional view in which the boundary between the region E1 and the region E2 is a section where the heights of the protruded lines and recessed lines 12 from the base part 13 (heights of the protruded lines from the base part) appear. The height of the protruded lines and recessed lines 12 from the base part 13 (that is, the heights H1 and H2 of the protruded line parts of embossment from the base part 13) can be selected, for example, from 0.14 mm to 0.3 mm.

The 3D patterned sheet constituted as described above can be produced by engraving the grooves corresponding to the protruded lines and recessed lines 12 of the 3D patterned sheet onto the embossing roll with laser and heating a sheet material before providing the 3D pattern while the sheet is sandwiched between the embossing roll and a supporting roll.

The 3D patterned sheet used as the support of the adhesive patch according to the present invention has different heights of the protruded lines and recessed lines 12 from the base part 13 (the heights of the protruded lines from the base part) depending on the region, and thus the texture and rigidity (flexibility) are different and logos, symbols, and the like can be indicated in a specific area. Therefore, a 3D patterned sheet is prepared so as to have a required texture and rigidity (or flexibility) at desired parts in the adhesive patch and to have the logos, medicinal names, or the symbols indicating them in specific regions. This 3D patterned sheet can be used as the support of the adhesive patch. As the heights of the protruded lines and recessed lines 12 from the base part 13 (the heights of the protruded lines from the base part) are higher, solidification by heating appears more obviously. And the region having high rigidity in the support can be made.

In the above aspect (refer to FIG. 4 and FIG. 5), the regions are determined to be four regions and the number of the different heights of the protruded lines and recessed lines 12 from the base part 13 (the heights of the protruded lines from the base part) is determined to be two. This, however, is merely an example. A plurality of regions can be employed and the number of the kinds of the heights can be determined to be three or more in the case where the number of the regions is three or more. As the method for forming the regions, the boundary line may be determined to be a horizontal line or regions may be provided in a mesh shape using horizontal lines and vertical lines as the boundary lines. The boundary line may be an oblique line or may be not limited to the straight line and may be a curved line. The heights of the protruded lines and recessed lines 12 from the base part 13 (the heights of the protruded lines from the base part) may be continuously varied instead of dividing the regions as illustrated in the above aspect (FIG. 5).

In the 3D patterned sheet used as the support of the adhesive patch according to the present invention, the physical parameters of the 3D patterned sheet such as the widths W with respect to the protruded lines and recessed lines 12, the inclination angles θ, the densities of the lines formed by the protruded lines and recessed lines 12, and a heating temperature in the processing may be set and used in addition to the heights of the protruded lines and recessed lines 12 (the heights of the protruded lines from the base part).

For example, the width W serving as the parameter refers to a variable representing the width of the protruded lines in a part of protruded lines and recessed lines 12 in one figure (that is, the width of the protruded line part of the linear embossment) as illustrated in FIG. 6. The density of the lines formed by the protruded lines and recessed lines 12 serving as the parameter refers to a variable which shows, for example, the number of lines of the protruded lines and recessed lines 12 which are included in the unit length (that is, the number of the protruded lines in the linear embossment per unit width, so to say, a parameter reflecting the width of the protruded line parts and the width of the recces parts).

In another aspect of the 3D patterned sheet, at least one of these physical parameters may be different from each other toward a predetermined direction (in the adjacent regions) in the sheet.

As the width W serving as the parameter becomes wider, the rigidity of the part may increase more. For example, the width W may theoretically be selected between 10 mm and 500 mm and suitable between 50 mm and 200 mm.

As the density of the lines serving as the parameter becomes higher, the rigidity may increase.

As the inclination angle serving as the parameter becomes smaller, the rigidity may increase more.

As the heating temperature in the processing (that is, the temperature in emboss processing while the sheet material sandwiched between the embossing roll and the supporting roll as described above) serving as the parameter becomes higher, the rigidity may increase more.

In one aspect of the 3D patterned sheet, the heights of the protruded lines and recessed lines 12 from the base part 13 (the heights of the protruded lines from the base part) are usually determined to be, for example, 0.14 mm to 0.3 mm as described above. The 3D patterned sheet in which the surface of the side on the embossing roll is determined to be the front surface can be obtained by using the embossing roll having the groove corresponding to this height and the supporting roll and heating a sheet before processing while the sheet is sandwiched between these two rolls. In this case, the pattern is generated on the front surface side of the sheet. The pattern, however, may also be generated on the back surface depending on processing conditions. In the adhesive patch according to the present invention, which is the final product produced using the produced 3D patterned sheet, the back surface of the sheet is desirably flat. In accordance with a method for obtaining the 3D patterned sheet having a flat back surface, a 3D patterned sheet in which the design (the pattern) is prevented from appearing on the back surface can be produced by adjusting at least one of the pressures between the embossing roll and the supporting roll, the processing speed (the rotation speed of the rolls), and the processing temperature or adjusting the depth of the groove on the embossing roll to be shallow.

The depth of the engraving in the engraved roll (embossing roll) for preventing the design (pattern) from appearing on the back surface as described above can be adequately selected within the range of, for example, 0.14 mm to 0.3 mm.

The aspect illustrated in FIG. 4 described above is an aspect in which the heights of the protruded lines and recessed lines 12 from the base part 13 (the heights of the protruded lines from the base part) are varied in the four regions. For example, as illustrated in FIG. 7, the 3D patterned sheet in which relatively soft texture in the regions E11 and E13 compared with the texture in the region E12 is obtained, whereas relatively hard texture in the region E12 compared with the texture in the regions E11 and E13 is obtained can be produced by dividing the sheet into three regions of the regions E11, E12, and E13, varying the engraving depth in the engraved roll to 0.14 mm in the regions E11 and E13 and to 0.3 mm in the region E12 to carry out emboss processing. The difference in these textures depends on the difference in rigidity and can be detected as a difference in a drape coefficient (bending resistance) measured by, for example, a test in accordance with a drape coefficient method.

Considering the use as the support of the adhesive patch according to the present invention, that is, considering a handling property during using the adhesive patch and skin followability during application, the drape coefficient of the 3D patterned sheet is preferably, for example, 0.1 to 1.0 (in accordance with JIS L 1096 method G (drape coefficient method)) or the like.

Examples of the various sheet materials for the materials of the 3D patterned sheet include paper such as impregnated paper, coated paper, high-quality paper, kraft paper, Japanese paper, and glassine paper; cellophane sheets and films; synthetic resin sheets and films such as films and sheets constituted by including a polyester-based resin such as polyethylene terephthalate and polybutylene terephthalate, a polyamide-based resin, an acetyl cellulose-based resin, a polylactic acid-based resin, a polyolefin-based resin such as polyethylene and polypropylene, a polyvinyl chloride-based resin, and a polycarbonate-based resin; the foamed material of a synthetic resin; a textile fabric such as a knitted fabric (also referred to as a knitted cloth), woven fabrics (also called a textile and a woof), and nonwoven fabrics; a leather cloth; and a laminate of two or more of these materials.

Out of these materials, the knitted fabric, the woven fabric, or the nonwoven fabric made of fibers of thermoplastic resins selected from the group consisting of the polyester-based resin such as polyethylene terephthalate and polybutylene terephthalate, the polyamide-based resin such as 6,6-nylon and 6-nylon, the acetyl cellulose-based resin such as triacetyl cellulose, and the polylactic acid-based resin are preferably used as the support.

For example, a knitted fabric that is a cloth knitted into a circular knitted fabric (interlock=both sides knit) using polyester-based fiber 100% processed yarn and has a product basis weight (also referred to as a mass per unit area or an area density) of about 95 g/m$^2$ to about 110 g/m$^2$ can be used as the material. This sheet cloth has a structure knitted with a double knitting machine. The sheet cloth is characterized in that the knitted stitches of a three-dimensional structure overlap each other and thus the sheet cloth has clogged knitted stitches, large elasticity, and excellent stability.

Alternatively, a flat woven fabric having a product basis weight of about 150 g/m$^2$ to about 200 g/m$^2$, a woven-knitted fabric having a thickness of 2 mm or smaller, or the like can be used.

In particular, as the material of the 3D patterned sheet, for example, a knitted fabric, a woven fabric, and a nonwoven fabric including at least polyester-based fibers such as polyester and modified polyester as fiber materials can be suitably employed. The sheet material (the knitted fabric, the woven fabric, and the nonwoven fabric) may include fiber materials in addition to the polyester-based fibers. Examples of such fiber materials include fiber materials made of thermoplastic resins such as polyolefin-based fibers (such as polyethylene-based fibers and polypropylene-based fibers), acetyl cellulose-based fibers (such as triacetate-based fibers), polyamide-based fibers (such as 6,6-nylon fibers and 6-nylon fibers), and polyvinyl chloride-based fibers.

From the viewpoint of the support of the adhesive patch, these knitted fabric, woven fabric, and nonwoven fabric, for example, the knitted fabric, woven fabric, and nonwoven fabric having a product basis weight of 70 g/m$^2$ to 120 g/m$^2$ and preferably 85 g/m$^2$ to 105 g/m$^2$ or the knitted fabric, woven fabric, and nonwoven fabric having a thickness of 0.6 mm to 1.2 mm and preferably 0.75 mm to 0.95 mm, are suitably used as materials for the 3D patterned sheet.

Pressure-Sensitive Adhesive Layer

The pressure-sensitive adhesive layer is a sticky layer in which various active components such as medicines and transdermal absorption promoters are supported as desired. The pressure-sensitive adhesive layer may be constituted of a single layer or may be constituted of a plurality of layers, if desired. In the case where the pressure-sensitive adhesive layer is constituted of a plurality of layers, the pressure-sensitive adhesive layer can be a laminated layer formed by laminating a layer including a medicine and a pressure-sensitive adhesive and a layer including the pressure-sensitive adhesive (not including a medicine).

In the case where a cataplasm is employed as the formulation of the adhesive patch, the pressure-sensitive adhesive layer (also referred to as a plaster layer) is preferably a layer made of a sticky hydrogel or the like. The thickness of the layer and the viscosity of the gel are adequately selected depending on the purpose.

As the sticky hydrous gel, a gel used as the plaster of a conventional adhesive patch can be used. For example, one or more water-soluble polymers such as sodium alginate, gum arabic, gelatin, pullulan, pectin, polyvinyl pyrrolidone, polyvinyl alcohol, methyl cellulose, ethyl cellulose, sodium carboxymethyl cellulose, hydroxyethyl cellulose, hydroxypropyl cellulose, a polyacrylic acid, sodium polyacrylate, an acrylic acid copolymer, a maleic anhydride copolymer, and methyl vinyl ether are used as a main raw material. A hydrous gel made by kneading a curing agent, a curing regulator, a mineral powder, a perfume, a pigment, water, and the like with this main raw material can be used. Each of the raw materials is adequately blended in an amount in such a degree that effects provided by the blend are sufficiently achieved and that quality deterioration and deterioration in use feeling, difficulty in handling in production, and the like due to excessive blend do not occur.

Preferable examples of various active components include transdermal absorbable medicines such as analgesics or antiinflammatory agents, coolants, and moisturizers. These active components may be used singly or in combination of two or more of the active components. Each of these medicinal components is adequately blended in an amount in such a degree that medicinal effects provided by the blend are sufficiently achieved and skin irritation and the like due to excessive blending may not occur.

In the case where a plaster agent is employed as the formulation of the adhesive patch, the pressure-sensitive adhesive layer may be constituted by including an adhesive and a tackifying resin selected from a synthetic rubber-based pressure-sensitive adhesive such as a styrene-isoprene-styrene block copolymer, a natural rubber-based pressure-sensitive adhesive, a hydrogenated petroleum resin, a rosin, a hydrogenated rosin, a terpene resin, an acrylic pressure-sensitive adhesive, and a silicone-based pressure-sensitive adhesive. To the pressure-sensitive adhesive layer, liquid rubbers such as polybutene and polyisobutylene, softening agents (plasticizers) such as liquid paraffin, vegetable oil, and lanolin, percutaneous absorption promoters such as fatty acid esters and higher alcohols, and ultraviolet absorbers may be further blended, if necessary.

As the various active components, the components described in the above <cataplasm>can be adequately blended.

Release Liner

The release liner is adequately selected depending on the purpose in consideration of easy peelability from the pressure-sensitive adhesive layer, air permeability, water permeability, flexibility, and the like. In general, preferable examples of the material of the release liner include a plastic film of polypropylene, polyethylene, polyester, polyurethane, polyvinyl chloride, polystyrene, polyethylene terephthalate, or other plastics; a plastic film obtained by subjecting one side or both sides of the plastic film to silicone processing; silicon-processed paper processed with silicon on a synthetic resin, synthetic paper, and synthetic fibers; aluminum foil; laminated paper formed by laminating kraft paper with polyethylene and the like that are colorless or colored. The material of the release liner may be used singly or in combination of two or more of the materials.

The thickness of the release liner is adequately selected depending on the material property and the like. An excessively thick release liner tends to be easily released from the plaster layer, whereas an excessively thin release liner tends to be easily damaged. Therefore, the thickness should be carefully determined. Usually, the thickness of the release liner may be preferably determined to be 10 µm to 100 µm. The shape of the release liner may be a rectangle with rounded corners, a circle, and the like. The size of the release liner is the same as the size of the support provided with the pressure-sensitive adhesive layer or slightly larger.

In order to facilitate the release of the release liner from the pressure-sensitive adhesive layer, the release liner may be subjected to surface treatment such as emboss processing.

In order to describe and illustrate the mark for peeling and/or the kind of the adhesive patch and the method for attaching the adhesive patch, figures such as arrows, character strings, and symbols may be printed on the release liner or the release liner may be colored.

The adhesive patch according to the present invention can be produced by production methods known in the art such as a method for forming the pressure-sensitive adhesive layer on the surface opposite to the surface on which the pattern of protruded lines and recessed lines of the support (3D patterned sheet) is formed, and laminating the release liner on the formed pressure-sensitive adhesive layer or a method for forming the pressure-sensitive adhesive layer on the release liner, and laminating the support (3D patterned sheet) to pressure-sensitive adhesive layer on the surface of the support opposite to the surface having the pattern of the protruded lines and recessed lines of the support.

In the adhesive patch targeted by the present invention, the same shape and size as those of conventional adhesive patches can be employed and various shapes and sizes can be selected depending on the attachment site (application site). Out of these shapes, the adhesive patch according to the present invention preferably has a rectangular shape having a longitudinal/width length ratio of 1/1 to 10/1.

EXAMPLES

Hereinafter, the present invention will be described more specifically with reference to Examples. The present invention, however, is not limited to Examples in any case.

Example 1 to Example 7

Preparation of Adhesive Patch

A knitted cloth that is a cloth knitted into a circular knitted fabric (interlock) using polyester-based fiber 100% processed yarn and has a product basis weight of 100 g/m² was used as the material. Each of the 3D patterns illustrated in FIG. 8 to FIG. 13 was transferred to one surface of the knitted cloth using an embossing roll to prepare 7 kinds of 3D patterned sheets. These 3D patterned sheets were used as supports.

A pressure-sensitive adhesive layer was provided on the surface of the support opposite to the side on which the 3D pattern was formed, and a release liner was laminated so as to cover the surface of the pressure-sensitive adhesive layer to prepare an adhesive patch having a size of 14 cm×10 cm.

Example 1 (FIG. 8): An aspect in which a 3D pattern is formed by dividing a substantially square into four triangles the apexes of each of which headed to upward, downward, left, and right directions, determining this substantially square region to be a one-unit figure, and forming a plurality of protruded lines in the figures of each of the triangles in a one-unit figure (refer to FIG. 2).

Example 2 (FIG. 9): An aspect in which a 3D pattern is formed by arranging a plurality of figures having various approximately polygonal shapes and forming a plurality of protruded lines in the figures so as to obtain a visual effect such that the approximately semicircular arcs are arranged in the longitudinal direction (left to right direction in FIG. 9).

Example 3 (FIG. 10): An aspect in which a 3D pattern is formed by providing a plurality of figures having various shapes, forming protruded lines such that respective lines are parallel with each other in each of the figures, and proving the protruded lines so that the directions of the protruded lines are different from each other in adjacent figure and, in some figures, forming protruded lines so that the inclination angles formed by the base part (front surface) and the walls of the protruded lines have an inclination angle different from the inclination angles in other figures in the formation of the protruded lines (refer to FIG. 1).

Example 4 (FIG. 11): An aspect formed by dividing the entire support into three regions, continuously forming the straight protruded lines at equal intervals so as to be parallel to each other in left and right regions, and forming character strings of "LEAD CHEMICAL" as one unit so as to be protruded parts aligned at substantially equal intervals in the center area.

Example 5 (FIG. 12): An aspect formed by dividing the entire support into three regions, continuously forming the straight protruded lines at equal intervals so as to be parallel to each other in the left and right regions, and forming character strings of "LEAD CHEMICAL" as one unit so as to be recessed parts aligned at substantially equal intervals in the center area.

Example 6 (FIG. 13): An aspect formed by dividing the entire support into three regions, continuously forming the straight protruded lines at equal intervals so as to be parallel to each other in the left and right regions and forming character strings of "LEAD CHEMICAL" as one unit so as to be recessed parts aligned at substantially equal intervals, and forming character strings of "LEAD CHEMICAL" as one unit so as to be recessed parts aligned at substantially equal intervals in the center area.

Example 7 (FIG. 14): An aspect formed by providing a plurality of figures having various polygon shapes, partitioning each of the figures with a linear region where no protruded lines are formed, providing the protruded lines within each of the figures so that the lines are parallel to each other, providing the orientations and widths of the protruded lines in different directions from each other through the boundary in the adjacent figures and arranging character strings of "(LOGO) LEAD CHEMICAL CO., LTD" as one unit in parallel at substantially equal intervals to each other on a part of the sheet to form protrusion and recess parts.

Bending Resistance Measurement Test

In the support (knitted cloth) provided with the 3D pattern, two kinds of sheets were prepared by varying the processing condition (processing temperature: 180° C. or 190° C.) of the patterning of the 3D pattern design illustrated in FIG. 10 and the bending resistances (drapability) of the two sheets were measured.

For the measurement of the bending resistance, JIS L 1096 method G (drape coefficient method) was employed. The test was carried out for the original cloth and the processed clothes (a processed cloth at 180° C. and a processed cloth at 190° C.). The results are listed in Table 1.

TABLE 1

|  | Original cloth | Cloth processed at 180° C. | Cloth processed at 190° C. |
| --- | --- | --- | --- |
| Drape coefficient | 0.121 | 0.182 | 0.222 |

The results listed in Table 1 indicate that the bending resistance (drapability) of the 3D patterned sheet is capable of being changed by varying the processing condition (temperature condition) in the 3D processing.

DESCRIPTION OF THE REFERENCE NUMERALS

10 Sheet
11 (11a and 11b) Figure
12 (12a and 12b) Protruded Lines and Recessed Lines
13 Base Part
14 Boundary
15 Boundary Line
16 Collection Point
E1, E2, E3, E4, E11, E12, and E13 Region
A Boundary
L1, L2, and L3 Line
H1 and H2 Height

The invention claimed is:

1. An adhesive patch comprising:
a support;
at least a pressure-sensitive adhesive layer provided on the support; and
a release liner attached on the pressure-sensitive adhesive layer so as to cover the surface of the pressure-sensitive adhesive layer, wherein
the support is a 3D patterned sheet comprising a plurality of areas, each area separated between adjacent areas by a boundary or a boundary and an edge of the sheet, and characterized by protruded lines and recessed lines parallelly and linearly extending between the boundaries encompassing the area or a boundary and the edge of the sheet,
the protruded lines and recessed lines remaining parallel to each other but having different directions in adjacent areas,
walls of the protruded lines and recessed lines in some of the areas are formed to be inclined by different inclination angles with respect to a base part, and
the protruded lines have different heights from the base part, serving as physical parameters of the protruded lines and recessed lines, toward a predetermined direction in the sheet.

2. The adhesive patch according to claim 1, wherein the physical parameters of the 3D patterned sheet are constituted of widths of the protruded lines and recessed lines, the inclination angles, densities of the lines formed by the protruded lines and recessed lines, and a heating temperature in 3D pattern processing in addition to the heights of the protruded lines, and at least one of the physical parameters is different from each other.

3. The adhesive patch according to claim 1, wherein the 3D patterned sheet is divided into a plurality of regions toward a predetermined direction in the sheet, and at least one of the physical parameters is different from each other in adjacent regions.

4. The adhesive patch according to claim 1, wherein the 3D patterned sheet is divided into a plurality of regions by line segments orthogonal in the surface of the sheet to a line heading toward a predetermined direction in the sheet.

5. The adhesive patch according to claim 1, wherein the 3D patterned sheet is formed so that one surface of the sheet is determined to be a front surface and the other surface is determined to be a back surface, the front surface having a pattern formed by protruded lines and recessed lines, the back surface being smooth, and the pressure-sensitive adhesive layer being provided on the back surface.

6. The adhesive patch according to claim 1, wherein the support including the 3D patterned sheet is formed of a knitted fabric, a woven fabric, or a nonwoven fabric made of fibers of at least one thermoplastic resin selected from the group consisting of a polyester-based resin, a polyamide-based resin, an acetyl cellulose-based resin, and a polylactic acid-based resin.

* * * * *